United States Patent [19]

Schuler et al.

[11] 4,295,857

[45] Oct. 20, 1981

[54] PROCESS FOR THE CRYSTALLINE PRECIPITATION OF CHROMOGENS

[76] Inventors: Peter Schuler, Am Knie 7, 8000 München 60, BRD; Erwin Braun, Unteranger 1, 8132 Tutzing, BRD, both of Fed. Rep. of Germany

[21] Appl. No.: 136,911

[22] Filed: Apr. 3, 1980

[30] Foreign Application Priority Data

Apr. 6, 1979 [DE] Fed. Rep. of Germany ....... 2913889

[51] Int. Cl.[3] ........................ B01D 9/02; G01N 33/15

[52] U.S. Cl. .................................. 23/301; 23/295 R; 23/300; 260/707; 427/2

[58] Field of Search ..................... 23/295 R, 300, 301, 23/230 B; 260/707; 427/2, 398.1; 128/760

[56] References Cited

U.S. PATENT DOCUMENTS 3,898,982 8/1975 Katsuda .............................. 128/760

4,045,125 8/1977 Weber .............................. 23/230 B

*Primary Examiner*—Bradley Garris

*Attorney, Agent, or Firm*—Hopgood, Calimafde, Kalil, Blaustein & Judlowe

[57] ABSTRACT

The invention contemplates a process for the crystalline precipitation of a chromogen from solution thereof in a solvent and within a capillary. The process involves first initiating a course of crystalline precipitation of the chromogen by initially and locally supersaturating the solution within the capillary, and thereafter evaporating the solvent at a rate and in an environment sufficient for further crystallization to proceed unimpeded by local supersaturation.

19 Claims, No Drawings

PROCESS FOR THE CRYSTALLINE PRECIPITATION OF CHROMOGENS

This invention relates to a process for the precipitation by crystallization of chromogens, particularly for clinical-chemical determinations.

BACKGROUND OF THE INVENTION

Upon the determination of the concentration of metabolism parameters from body fluids in the field of clinical chemistry, an exact volumetric dosaging of sample and of dissolved reagents plays a decisive role. Generally there are employed for this dosaging aids of the type of pipettes which may depending on their nature, be glass or plunger pipettes, or fully or partially automated dosaging devices. These aids have the disadvantage that they are of high cost; they furthermore require continuous supervision in the sense of calibration verification in order to assure the correctness of the volume of liquid dosed. In the case of partially automatic and manually actuated systems the possibility of errors in operation can furthermore not be excluded so that operation by non-skilled personnel is out of the question.

It has therefore been successfully attempted to avoid the above-described difficulties by preportioning the individual components of the reagent mixture depending on the resultant stability, either in pure form or as partial mixture, and thus doing away with the necessity of pipetting steps for the user. For the dosaging of the specimen (blood, serum or plasma) there can furthermore be used a so-called end-to-end capillary which automatically fills itself on basis of capillary forces, whereby the danger of errors in dosaging can be excluded, or at least reduced.

If a reagent component or a mixture of several components is stable in solution, then the preportioning can be effected by provision of a volume of liquid supplied by machine. For this there is suitable, for instance, the buffer solution, which can advantageously be introduced directly into the measurement cell. Such a method, which in addition employs a specimen capillary is described in DE-OS 24 22 260 (West German Unexamined Application for Patent).

A pre-portioning, however, affords difficulties with respect to preparation if individual components are used in only very small quantities, such as enzymes, coenzymes or chromogens. One way out of this difficulty is to mix the small amounts of active substance with a larger amount of inert filler and to work the mixture into a tablet, which can then be handled more easily.

However, this method of preparation is not without problems with respect to the dissolving time of the tablet and possible losses of active substance—for instance loss of enzymatic activity—upon the compressing of the mixture to form the tablet. It furthermore presupposes that the active substance be available, stable, in solid form, which is not always true, particularly in the case of enzymes—for example cholesteroloxidase.

In order to solve these difficulties it has been proposed to include such small amounts of substance in a solvent, fill a capillary with the resultant solution, and precipitate the substance by evaporating the solvent in the capillary. Such a coated capillary represents a particularly advantageous form of administration of the reagent component since it makes it possible easily to handle even very small amounts of substance without addition of fillers, which might prove disturbing. One method of this type is described in DE-OS 27 21 942 (West German Unexamined Application for Patent).

The coated capillaries must satisfy a number of requirements the satisfying of which is of importance for the possibility of use or the range of use. Thus the substance must be deposited in stable form without the active substance spoiling. The process must furthermore assure a readily reproducible coating with respect to the amount of substance and be suited for industrial mass production. Finally, it is advantageous for the capillary to be still absorptive even after the coating, so that it can be used for the dosing of further reagent components, for instance a liquid enzyme suspension.

The satisfying of these requirements encounters difficulties, particularly furthermore in the case of an important chromogen of clinical chemistry, namely 4-aminophenazone. Thus this substance tends to deposit from a large number of solvents upon evaporation of the solvent not in crystalline form but as an amorphous oil. The oil obtained begins to solidify after a short period of time forming a yellow color, and a resinous hydrophobic layer is produced by which the capillary loses its absorption capacity. The yellow coloration of the substance expresses itself in a new band in the absorption spectrum and has a disturbing effect on photometric measurement due to the occurrence of high reagent blank values. If the conditions under which the solvent is evaporated are varied, for instance by applying a vacuum, it is, it is true, possible in individual cases to obtain a finely crystalline precipitation with good absorptivity but it is found that these results are of uncertain reproducibility, so that mass production is not thereby possible.

Another difficulty is that even if a crystalline precipitation having in principle good adsorption properties is obtained, the substance may not deposit in a homogeneous layer but rather as a plug at one end of the capillary, whereby the capillary is closed up and therefore is no longer adsorptive.

The known method of freeze-drying is not suitable for overcoming the above-indicated difficulties since, when using capillaries, it is very difficult to maintain the frozen condition—necessary for success—during the entire course of the process. Due to their low heat capacity the capillaries on the one hand tend, after the freezing, to thaw again already on their path to the deep-freezing unit while, on the other hand, the ratio of heat capacitance to energy of sublimation withdrawn from the dry material is so unfavorable that without special cooling it is impossible to prevent thawing of the content of the capillary during the drying itself. Such additional cooling measures—such as for example the use of a cooled setting surface—are however difficult to employ, due to the unfavorable shape of the capillaries and the fact that they are open at both ends, so that freeze-drying as a whole does not provide an answer.

BRIEF STATEMENT OF THE INVENTION

The object of the invention is to eliminate the problems described above and to create a simple process which permits, without special expense, a homogeneous, crystalline, readily-reproducible precipitation of chromogens, particularly 4-aminophenazone, in capillaries with retention of the absorptivity and which is suitable for mass production.

This object is achieved in accordance with the invention by initiating a course of crystalline precipitation of a chromogen from a solvent solution thereof within a capillary, by initially and locally supersaturating the solution within the capillary, and by thereafter evaporating the solvent at a rate and in an environment sufficient for further crystallation to proceed unimpeded by local supersaturation.

The initial supersaturation can be obtained in various manners. In one preferred embodiment of the process of the invention, a solvent mixture of a chromogen-dissolving component and a non-chromogen dissolving component is used, a predetermined amount of chromogen being treated with just a sufficient amount of the dissolving component to produce complete solution and the condition of initial supersaturation being obtained by adding a suitable amount of the non-dissolving component.

This preferred embodiment is of particular advantage for use in clinical chemistry. Generally it is desired therein to precipitate a very specific amount of chromogen in a capillary of predetermined volume so that for the filling of the capillary there must be used a solution which has this ratio of chromogen content to volume, i.e. has a given concentration. When a solvent mixture of the type described is used there is now the possibility, in contradistinction to a pure solvent, of combining this predetermined concentration within wide ranges with a desired degree of supersaturation depending on what amount of the non-dissolving component is added.

An initial supersaturation can also be obtained and crystallization initiated by a reduction of the temperature of a solution containing the chromogen. A combination of the two measures can, in particular, be of special advantage, particularly if the chromogen starts to crystallize out already during the filling of the capillary as a result of the initial supersaturation, i.e. if the solution cannot be handled. In one particularly preferred embodiment of the process of the invention, therefore, by the use of a suitable amount of the non-dissolving component there is obtained only such a degree of saturation that the solution is stable or meta-stable at the temperature of formation and that by then decreasing the temperature, reaches a supersaturation so that crystallization commences.

After the initiating of the crystallization, the further course of precipitation takes place during evaporation of the solvent. In this connection, it is of particular importance for the process of the invention to avoid supersaturation since, surprisingly, it has been found that in this way the above-described formation of a plug at one end of the capillary can be avoided in a simple fashion. Supersaturation can occur, for instance if the solvent evaporates so rapidly that there is not sufficient time for unimpeded crystallization to an extent which corresponds to the rate of evaporation. With progressive evaporation there remains in the initially full capillary a short path of a strongly supersaturated solution which, due to the unavoidable slight inclining of the capillary, collects at one end and from which the plug is produced upon evaporation of the final traces of the solvent.

If a solvent mixture is used for the process of the invention it must be seen to it that the vapor pressures of the individual components are adapted to each other. In particular, one must avoid having the non-dissolving component being more readily volatile than the dissolving component since this would result in a strong undersaturation which would necessarily also lead to the formation of a plug.

The supersaturation can be prevented in various manners, the essential thing being to allow the evaporation to take place just sufficiently fast for an unimpeded crystallization to be possible.

Thus, for example, from a number of chemically homologous solvents having substantially the same dissolving properties with respect to the chromogen there can be selected the solvent with which the rate of evaporation at a given temperature has the required value.

In addition to the obtaining of an initial supersaturation, a given temperature can serve so to adjust the rate of evaporation of the solvent or solvent mixture that unimpeded crystallization is obtained.

The crystalline precipitation of the chromogen can be accelerated in known manner by the addition of crystallization seeds.

In practice, a combination of the above-mentioned measures has proven advisable. There is preferred here the use of a solvent mixture—consisting of a dissolving component and a non-dissolving component—in which the two components are each selected from a homologous series in such a manner that the rate of evaporation of the dissolving component is slightly greater than that of the non-dissolving component. At the same time it is seen to it, by a temperature of $-20°$ to $-50°$ C., that the evaporation as a whole does not take place too rapidly.

In this preferred embodiment of the process, crystallization seeds are furthermore introduced into the capillaries prior to the filling thereof, using for this, preferably, fine crystals of the chromogen itself.

For example, for the crystalline precipitation of 4-aminophenazone there has proven suitable as solvent mixture the combination of an alkyl alcohol as dissolving component and of a dialkyl either as non-dissolving component, the pair consisting of methanol and diisopropyl ether being particularly advantageous. A supersaturated solution which can be handled (i.e. is metastable at room temperature) is obtained if the solution contains about 2.95 vol.% methanol per 100 $\mu$g 4-aminophenazone. By introducing fine crystals of 4-aminophenazone into the empty capillaries crystallization is brought about immediately upon filling, and at $-50°$ C. the evaporation of the solvent mixture takes place just so fast that no plug is produced. The cooling in this connection to $-50°$ C. is preferably effected very rapidly, i.e. without any interim storage of the filled capillaries at room temperature.

In principle, one need not wait until the solvent or solvent mixture has completely evaporated and the chromogen has thus completely precipitated. If it is desired to precipitate only a given amount of chromogen, the process can also be interrupted by removing the balance of the liquid by absorption, for instance by means of filter paper. Complete evaporation, is however, preferred if special demands are made as to the reproducibility of the precipitated amount of chromogen from one capillary to the next. The aforementioned possibility of bringing any desired amount of chromogen into any desired initial supersaturation by a suitable composition of the solvent mixture is of particular advantage here.

There is furthermore particularly preferred an embodiment of the process in which the chromogen, after the precipitation, in order to increase its stability is freed of the last traces of solvent, i.e., after-dried, by applying a vacuum and possible use of a suitable drying agent.

Another advantage of the method of the invention is that there are obtained thereby homogenous crystalline layers which adhere so well to the inner wall of the capillaries that the precipitated substance does not flow off, even under the influence of strong mechanical vibrations. Results of this type cannot be obtained, for instance, by the method of freeze-drying—even if it could be carried out despite the difficulties described—since the precipitated substance is always obtained in the form of a loose thread of poor adherence to the inner wall which breaks up and drops down even upon only slight mechanical vibration. The method of the invention can thus be used to advantage wherever the coated capillaries must be able to withstand, without damage, vibrations of this type, such as are unavoidable, for instance, on the normal path of shipment to the consumer.

SPECIFIC EXAMPLES

In the examples described below, there is used to receive the capillaries a plastic wheel of a diameter of about 200 mm which is provided at its outer periphery with 48 identations within which the capillaries are held by means of an O-ring clamped around the periphery of the wheel. To manipulate a round plastic rod of a length of about 200 mm enables the wheel to be taken up via a borehole provided in the center of the wheel. Glass capillaries are used having a length of 32 mm and a volume of 10 $\mu$l.

The supersaturated 4-aminophenazone solution is pumped by a hose pump from a storage container into a filling station, which consists of a flat flow-bed from which the solution can flow off via a borehole and is conducted via a hose back into the storage container. The closure borehole is arranged at a given height above the bottom of the flow bed so that a constant level of liquid is maintained therein.

Upon the filling, the capillaries which are clamped on the wheel are dipped by manipulating the above-described rod at an angle of about 15°-30° obliquely into the traversed flow bed, and one capillary after the other is filled by slow rotation of the wheel.

The introduction of crystallization seeds into the capillaries—hereinafter referred to as "seeding"—can be effected in the following manner:

Finely ground 4-aminophenazone is spread out in a shallow petri dish in a layer thickness of about 2 mm. By dipping the capillaries clamped in the receiving wheel into this layer there is produced in one end of them a plug of 4-aminophenazone of a length of about 1 to 1.5 mm, which plug thereupon is distributed uniformly over the inner wall by blowing compressed air onto the capillaries at this end.

These mechanical aids, however, do not actually form an object of the process of the invention and therefore do not require any special explanation.

EXAMPLE 1

142 mg of 4-aminophenazone are dissolved completely in 700 $\mu$l of methanol and the resultant solution is brought to a volume of 10 ml by means of di-sec-butyl ether. After about 8×48 capillaries have been filled (8 wheels), the filled capillaries are subjected to a temperature of −50° C. by bringing them into a refrigerator. The crystallization of 4-aminophenazone commences within 15 minutes. After 24 hours the solvent has completely evaporated.

For the after-drying the capillaries are then introduced into a desiccator which contains active silica gel as drying agent, and a vacuum is applied to the desiccator by means of an oil rotary-slide-valve pump. After the final vacuum of about 1 mb has been reached, the pump is disconnected and the capillaries are after-dried for 4 hours under the action of the drying agent.

EXAMPLE 2

292 mg of 4-aminophenazone are dissolved in 860 $\mu$l of methanol and the resultant solution is made up to 20 ml with diisopropyl ether. For the filling there are used about 15×48 capillaries (15 wheels) which have been previously subjected to seeding in the manner described above. In this embodiment of the process, the crystallization of 4-aminophenazone commences immediately after the filling of the capillaries so that, for the reasons described, it must be seen to it that they are subjected immediately to a temperature of −50° C. by introduction into a refrigerator without any intermediate storage at room temperature. At the end of 2 hours the solvent has completely evaporated and the after-drying is effected in the manner described in Example 1.

For the determination of the content of the coated capillary the following method can be used:

From each wheel, 5 to 10 capillaries are taken in accordance with a sample size of 10.4 to 20.8%, and each of them is introduced into a test tube containing 10 ml of distilled water. By vigorous shaking, the deposited substance is brought into solution and the extinction of the resultant solution is measured photometrically against distilled water at a wavelength of 270 mm.

The method of the invention gives satisfactory results with respect to mass production. For example, the following typical measured values were found with the indicated test method in the embodiments thereof set forth in Examples 1 and 2.

| | Example 1 | Example 2 |
|---|---|---|
| Size of sample | 20.8% | 10.4% |
| Mean value of extinction | 0.55 | 0.58 |
| Standard deviation | 0.02 | 0.017 |
| Coefficient of variation | 3.6% | 2.8% |

The individual measurements in each case satisfied a normal distribution. The testing of the absorptivity with an enzyme suspension containing 4000 units of cholesterol oxidase per liter, 12,000 units of cholesterol esterase per liter and 16,000 units of peroxidase per liter gives absorption times of less than 7 seconds (Example 1, size of sample 20.8%) and less than 4 seconds (Example 2, size of sample 10.4%) respectively.

We claim:

1. A process for crystalline precipitation of a chromogen from solution thereof in a solvent and within a capillary, comprising the steps of initiating a course of crystalline precipitaton of the chromogen by initially and locally supersaturating the solution within the capillary, and thereafter evaporating the solvent at a rate and in an environment sufficient for further crystallization to proceed unimpeded by local supersaturation.

2. A process according to claim 1, characterized by the fact that, from a series of chemically homogolous solvents having substantially the same solution properties, solvent is selected having a rate of evaporation at a given temperature such that upon said further crystallization the solution no longer passes into a supersaturated condition during the entire further course of crystallization.

3. A process according to claim 1 or 2 characterized by the fact that a solvent mixture is used as solvent.

4. A process according to claim 3, characterized by the fact that the solvent mixture consists of a component which dissolves the chromogen and of a component which does not substantially dissolve the chromogen.

5. A process according to claim 4, characterized by the fact that such an amount of the chromogen-dissolving component is used as is necessary in order at least to dissolve a predetermined amount of chromogen and that the condition of initial supersaturation is obtained by adding a suitable quantity of the non-dissolving component.

6. A process according to claim 4, characterized by the fact that an ether is used as dissolving component.

7. A process according to claim 4, characterized by the fact that 4-aminophenazone is used as chromogen, a dialkyl ether is used as non-dissolving component, and methanol is used as dissolving component.

8. A process according to claim 7, characterized by the fact that the dialkyl ether is a symmetrical dialkyl ether having 1 to 5 carbon atoms per side chain.

9. A process according to claim 7, characterized by the fact that the dialkyl ether is diisopropyl ether.

10. A process according to claim 7, characterized by the fact that as dissolving component 2 to 6 vol. % methanol per 100 μg of 4-aminophenazone is used.

11. A process according to claim 7, characterized by the fact that 2.95 vol.% methanol per 100 μg of 4-aminophenazone is used.

12. A process according to claim 1, characterized by the fact that the temperature of the solvent for its evaporation is so selected that crystallization takes place but supersaturation is avoided.

13. A process according to claim 1, characterized by the fact that in order to avoid supersaturation upon the further crystallization the solution is brought to a temperature at which the solvent evaporates at a minumum rate such that unimpeded crystallization is achieved.

14. A process according to claim 13, characterized by the fact that the temperature is less than −30° C.

15. A process according to claim 13, characterized by the fact that the temperature is less than or equal to −50° C.

16. A process according to claim 13, characterized by the fact that the temperature is maintained until the solvent has completely evaporated.

17. A process according to claim 1, characterized by the fact that after the precipitation of the chromogen after-drying with the application of a vacuum is effected.

18. A process according to claim 1, characterized by the fact that crystallization seeds are introduced into the capillaries before they are filled with the chromogen-containing solution.

19. A process according to claim 18, characterized by the fact that fine crystals of the chromogen to be precipitated out are used as crystallization seeds.

* * * * *